(12) United States Patent
Spoof

(10) Patent No.: US 11,259,746 B2
(45) Date of Patent: Mar. 1, 2022

(54) METHOD AND SYSTEM FOR NEUROMUSCULAR TRANSMISSION MEASUREMENT

(71) Applicant: General Electric Company, Schenectady, NY (US)

(72) Inventor: Markku Erik Spoof, Jokela (FI)

(73) Assignee: General Electric Company, Schenectady, NY (US)

( * ) Notice: Subject to any disclaimer, the term of this patent is extended or adjusted under 35 U.S.C. 154(b) by 1071 days.

(21) Appl. No.: 15/646,005

(22) Filed: Jul. 10, 2017

(65) Prior Publication Data

US 2019/0008453 A1 Jan. 10, 2019

(51) Int. Cl.
*A61B 5/00* (2006.01)
*A61N 1/36* (2006.01)
*A61B 5/389* (2021.01)
*A61B 5/11* (2006.01)

(52) U.S. Cl.
CPC ............ *A61B 5/4848* (2013.01); *A61B 5/389* (2021.01); *A61B 5/4035* (2013.01); *A61N 1/36014* (2013.01); *A61B 5/1114* (2013.01); *A61B 5/4836* (2013.01)

(58) Field of Classification Search
None
See application file for complete search history.

(56) References Cited

U.S. PATENT DOCUMENTS

| | | | |
|---|---|---|---|
| 4,595,018 A | 6/1986 | Rantala | |
| 5,697,381 A | 12/1997 | Rantala et al. | |
| 6,389,312 B1 | 5/2002 | Duckert | |
| 7,496,400 B2 | 2/2009 | Hoskonen et al. | |
| 2002/0007129 A1* | 1/2002 | Marino | A61B 5/0488 600/546 |
| 2011/0098761 A1* | 4/2011 | Wittenberger | A61B 5/4035 607/1 |
| 2013/0204155 A1* | 8/2013 | Brull | A61B 5/1106 600/546 |
| 2014/0012157 A1* | 1/2014 | Gilhuly | G06F 19/00 600/554 |
| 2019/0223764 A1* | 7/2019 | Hulvershorn | A61B 5/7217 |

OTHER PUBLICATIONS

P. A. Stewart, Comparison of electromyography and kinemyography during recovery from non-depolarising neuromuscular blockade, 2014, Anaesth Intensive Care, 42, pp. 378-384 (Year: 2014).*
"Neuromuscular Transmission," GE Healthcare Website, Available Online at http://clinicalview.gehealthcare.com/download.php?obj_id=319&browser=true, Available as Early as Jan. 2017, 4 pages.

* cited by examiner

*Primary Examiner* — Sean P Dougherty
(74) *Attorney, Agent, or Firm* — McCoy Russell LLP

(57) ABSTRACT

Methods and systems are provided for monitoring neuromuscular blockade in patients during surgical procedures. In one embodiment, a system includes a stimulator, an electromyography (EMG) sensor, a kinemyography (KMG) sensor, and a single connector configured to couple each of the stimulator, the EMG sensor, and the KMG sensor to a patient monitoring device via a single input. In this way, neuromuscular transmission (NMT) monitoring in patient may be done reliably by ensuring that NMT measurement from a first sensor (EMG sensor) is in line with the measurement of the second sensor (KMG sensor).

13 Claims, 5 Drawing Sheets

METHOD AND SYSTEM FOR NEUROMUSCULAR TRANSMISSION MEASUREMENT

FIELD

Embodiments of the subject matter disclosed herein relate to medical devices, and more particularly, to monitoring neuromuscular transmission during a surgical procedure.

BACKGROUND

Neuro Muscular Transmission (NMT) is the transfer of an impulse between a nerve and a muscle in the neuromuscular junction. NMT may be blocked in a patient undergoing a surgical procedure, for example, by neuromuscular blocking agents/drugs, which may cause transient muscle paralysis and prevent the patient from moving and breathing spontaneously. Thus, the level of neuromuscular block may be monitored to ensure appropriate block is provided for the given procedure.

BRIEF DESCRIPTION

In one embodiment, a system includes a stimulator, an electromyography (EMG) sensor, a kinemyography (KMG) sensor, and a single connector configured to couple each of the stimulator, the EMG sensor, and the KMG sensor to a patient monitoring device via a single input. In this way, neuromuscular transmission (NMT) monitoring in patient may be done reliably by ensuring that NMT measurement from a first sensor (EMG sensor) is in line with the measurement of the second sensor (KMG sensor).

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
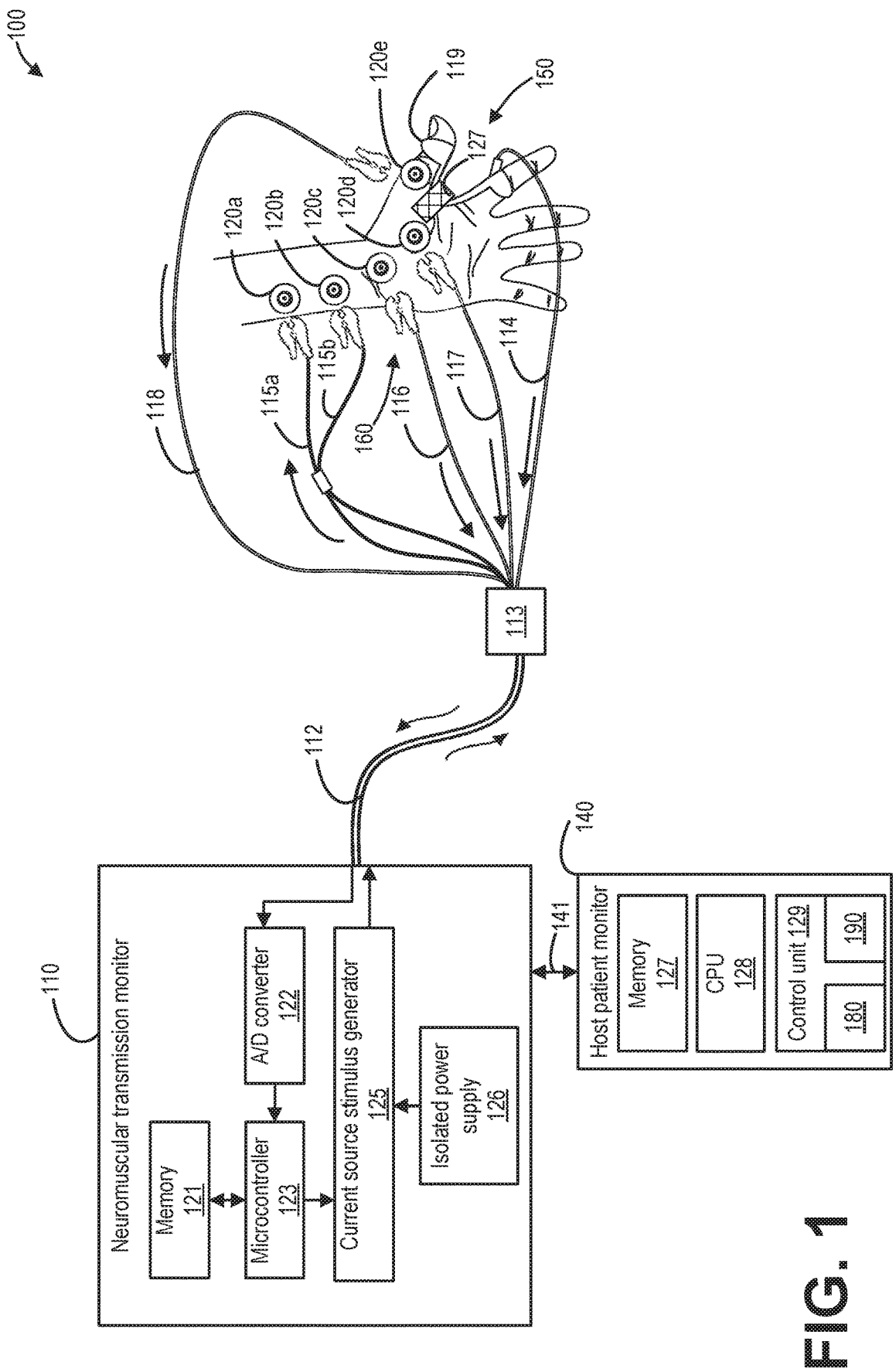
FIG. 1 shows an example neuromuscular transmission monitoring system.

The following description relates to various embodiments of a neuromuscular transmission (NMT) monitoring system configured to monitor an amount of neuromuscular blockage after the administration of muscle relaxants in patients during surgery. Neuro Muscular Transmission (NMT) is the transfer of an impulse between a nerve and a muscle in the neuromuscular junction. NMT may be blocked by neuromuscular blocking agents/drugs, which may cause transient muscle paralysis and prevent the patient from moving and breathing spontaneously. Additionally, muscle relaxation may be used during general anesthesia to enable endotracheal intubation and to provide the surgeon with optimal working conditions. At the end of a surgical procedure, the neuromuscular block is reversed such that neuromuscular activity may be returned to normal and that the patient may be able to breathe unassisted, before the removal of the endotracheal intubation (i.e. extubation). Thus, appropriate assessment of the degree of NMT block may be used for ensuring proper timing of intubation and for guiding intraoperative administration of neuromuscular blocking agents, maintaining a desired degree of intraoperative neuromuscular block, and ultimately preventing the occurrence of residual muscle paralysis.

An NMT monitor may be used to monitor muscle response to electrical stimulation of a motor nerve (e.g., ulnar nerve). For example, an electrical stimulus may be provided at the ulnar nerve near the wrist and the response of the muscle near the thumb, adductor pollicis, may be monitored. In clinical settings, a nerve stimulator is attached to a motor nerve of the patient and an electrical stimulation current is applied to the patient before induction of anesthesia. A baseline value for the muscle response is recorded by the NMT monitor and used to normalize the muscle response once the muscle relaxant is administered. The evoked muscle responses may then be monitored via several methods, including the measurement of electrical response of the muscle (electromyography (EMG)) and the measurement of the degree of distortion or bending in a piezoelectric film attached to the muscle (kinemyography (KMG)). In EMG, multiple electrodes may be used to record the compound muscle potential stimulated by the stimulus generator. However, small movements of the hand may alter the electrical signal since the electrode geometry may be different. Further, EMG responses may also be susceptible to the electrical noise and interference from other electrical devices (e.g., electrical motors, cautery devices, surgical microscopes, etc.) used in the operating room. In contrast, KMG measures electrical activity based on the distortion or bending of the piezoelectric polymer strip placed within the bending sensor between the thumb and forefinger. However, the sensor may not be sensitive enough to detect small movement during deep sedation.

Another short-coming of neuromuscular monitoring is that if the patient is already paralyzed and/or intubated, for example during an emergency procedure, then a baseline value for NMT may not be reliably collected, which may then lead to inaccurate muscle response measurement in the paralyzed patient during the surgical procedure. Furthermore, if muscle response is inaccurately measured, an overdose of muscle relaxant may be administered leading to residual paralysis in the patient. Further, inaccurate muscle response measurement may also lead to inadequate anesthesia monitoring, especially during monitoring the neuromuscular blockade recovery period, which may lead to the improper timing for extubation and/or incorrect timing of neuromuscular blocking agent (NMBA) antagonist administration. Thus, a more reliable and accurate muscle response measurements technique(s) may be needed for monitoring neuromuscular blockade in paralyzed patients.

Figure 2:
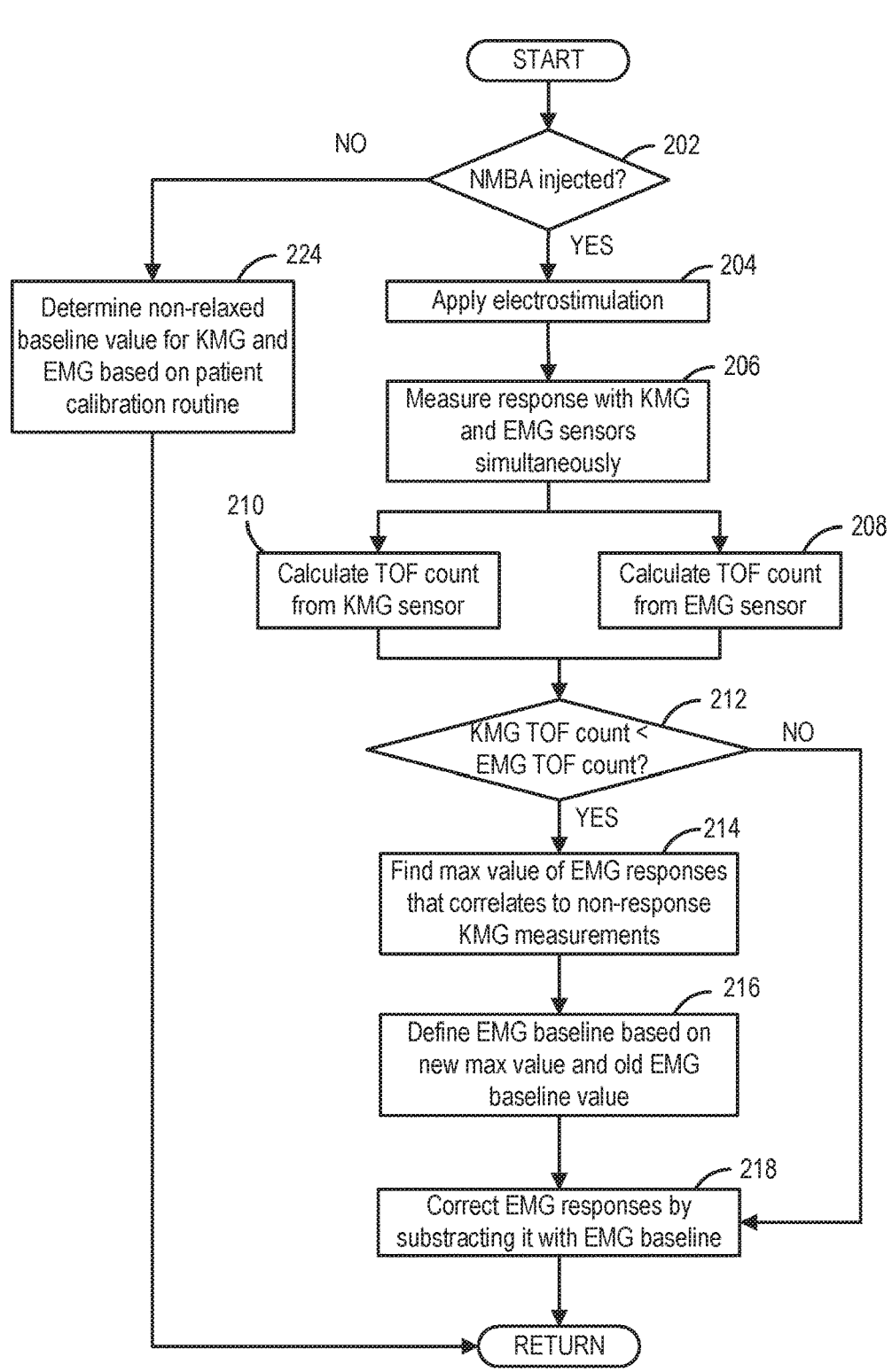
FIG. 2 shows a high-level flow chart illustrating an example method for establishing 'non-response' muscle activity baseline for neuromuscular monitoring system of FIG. 1.
Figure 3:
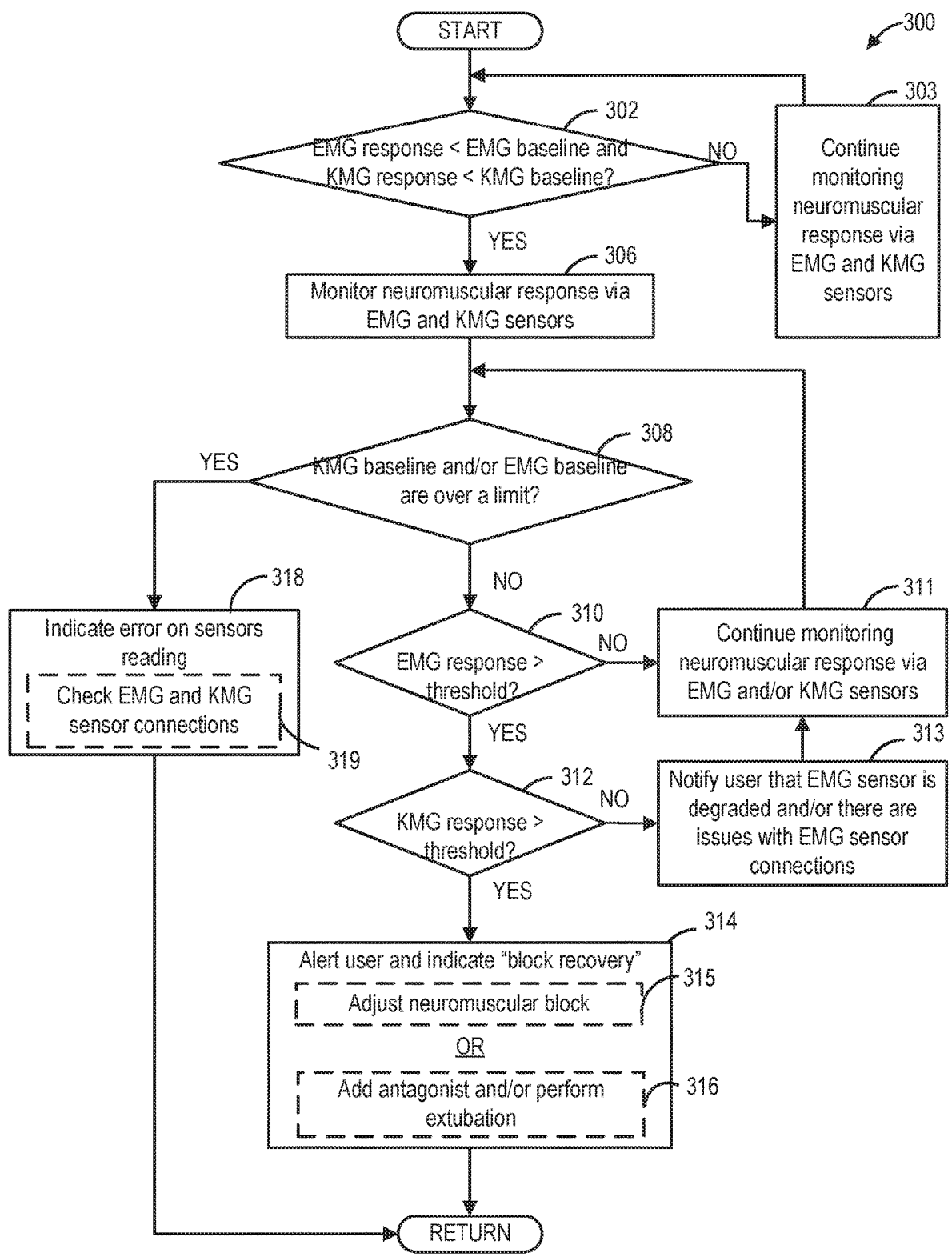
FIG. 3 shows a high-level flow chart illustrating an example method for monitoring the level of neuromuscular blockade in patients.
Figure 4:
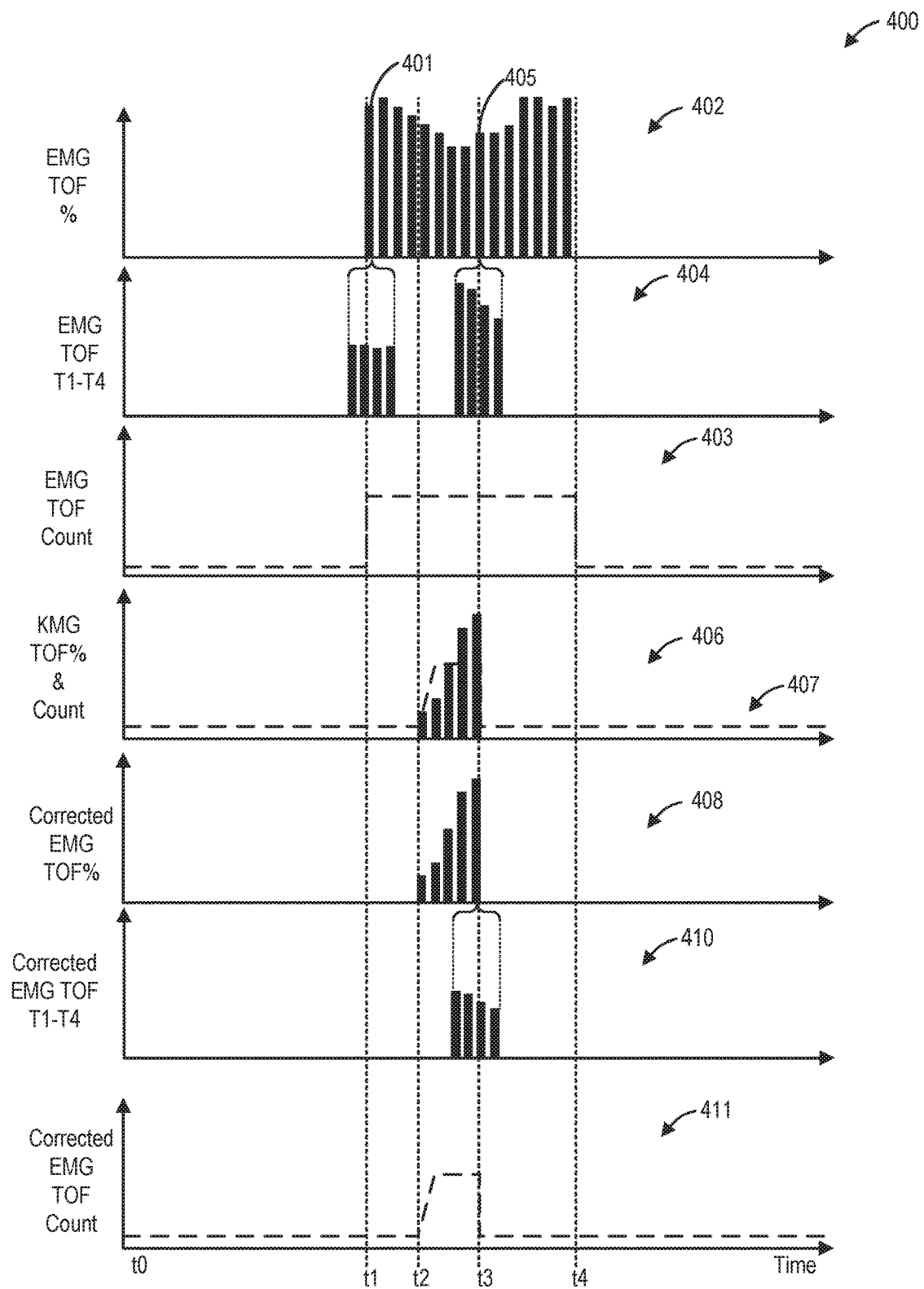
FIG. 4 shows an example timeline for correcting neuromuscular transmission output based on the non-response muscle activity baseline in patients.
Figure 5:
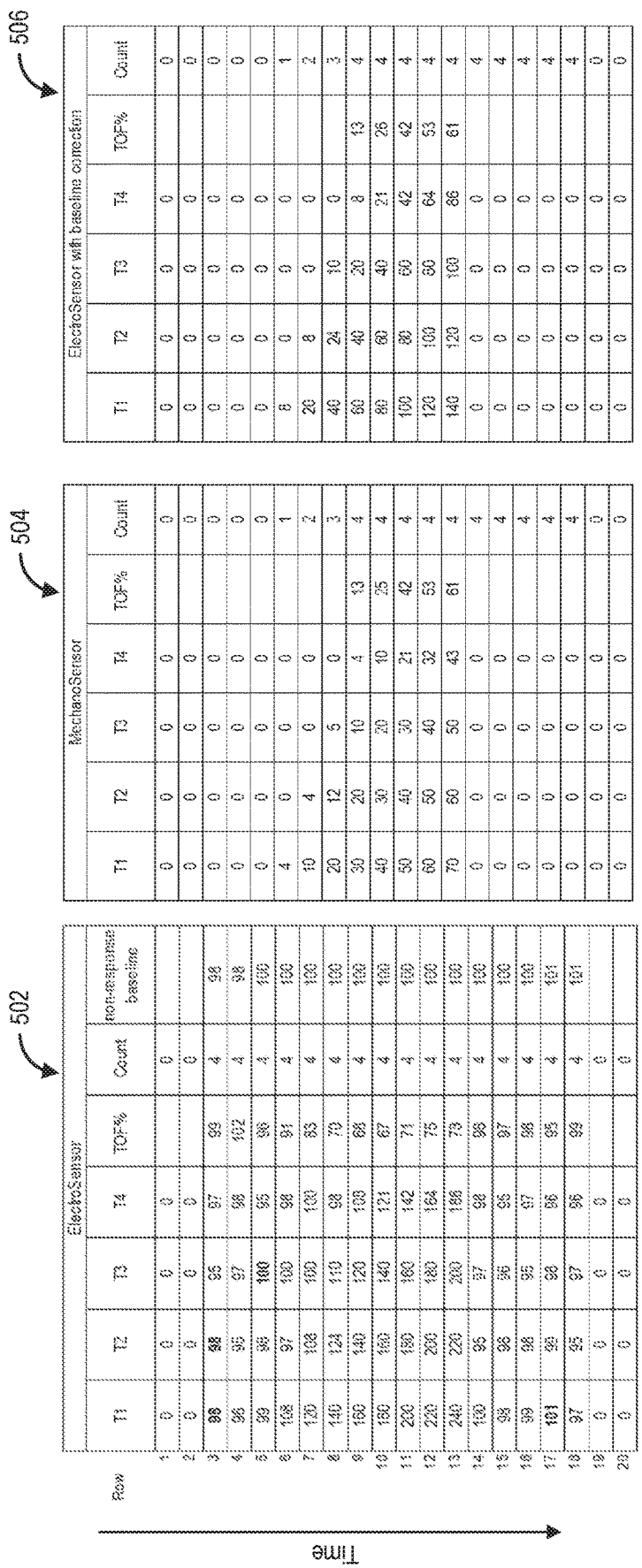
FIG. 5 shows an example raw output values of neuromuscular monitoring sensors.

According to embodiments disclosed herein, neuromuscular transmission monitoring may be performed by simultaneously measuring physical muscle movement via a kinemyography (KMG) sensor and by measuring the electrical potentials at the muscle via an electromyography (EMG) sensor, in response to an electric stimulation of a motor nerve. Further, the neuromuscular monitoring system may automatically set a "non-response" baseline value for the patient based on the measurements from KMG and EMG sensors. An example of a neuromuscular transmission monitoring system is provided in FIG. 1. The NMT monitoring system may include one or more mechano-sensors which detect movement of the muscle in response to nerve stimulation (referred to as a KMG sensor), one or more electro-sensors which detect electrical activity of a muscle (referred to as an EMG sensor) in response to nerve stimulation, and a single unit of nerve stimulator. The NMT monitoring system of FIG. 1 also includes a computing system including instructions to carry out one or more control routines for determining a muscle response baseline as well as monitoring neuromuscular block in patients during surgery. An example method for determining a non-response baseline for muscle activity in paralyzed patients may be carried out by the computing system of the NMT monitoring system of FIG. 1 is illustrated in FIG. 2. The NMT monitoring system may be further configured to measure muscle response and provide a user interface that may be displayed during surgical procedures as shown in FIG. 3. A prophetic neuromuscular transmission monitoring with EMG baseline correction based on the KMG non-response values is illustrated in FIGS. 4-5.

FIG. 1 illustrate an example neuromuscular transmission (NMT) monitoring system 100 that is configured to monitor neuromuscular activity via EMG and KMG techniques. NMT monitoring system 100 includes a neuromuscular transmission monitor 110 which is communicatively coupled to a host patient monitor 140 via a communication link 141. The neuromuscular transmission monitor 110 includes a plurality of neurostimulators, 115a and 115b, for providing stimulation output (e.g., electrical stimuli) of varying type and frequency to the patient and at least one input connected to one or more transducers for monitoring the evoked muscle response in response to the electrical stimuli provided by the neurostimulators. The transducers include an EMG sensor 160 consisting of a plurality of electro-sensors for measuring the action potential of muscle contraction in response to nerve stimulation and a KMG sensor 150 consisting of mechano-sensor for measuring muscle movement in response to nerve stimulation. The signals detected by the transducers may then be converted into electrical signals by the A/D converter 122 of neuromuscular transmission monitor 110.

In the depicted example, neurostimulators 115a and 115b are connected to stimulating electrodes 120a and 120b, respectively, which may apply an electrical stimulus to the patient's ulnar nerve at a pre-determined time interval. The amount of electrical stimulation provided to the neurostimulators is controlled by a current stimulus generator which receives command signals from microcontroller 123. Microcontroller 123 is linked to the user interface of control unit 129, which comprises of a display unit 190 and buttons/knobs 180. The type and frequency of the stimulation output may be adjusted manually by the user (manual mode) or be automatically chosen by the system (automatic mode). In one example, the type and frequency of the stimulation output may be adjusted by the user via pressing buttons or knobs 180 on the patient host monitor 140. In one example, neurostimulators 115a and 115b may be two wires of positive and negative charges, which may be attached by alligator clips to stimulating electrodes 120a and 120b on the skin of the patient's forearm.

A power supply (not shown) may supply electricity to an isolated power supply 126 which in turn provides power to current source stimulus generator 125. The microcontroller 123 may be connected to the current source stimulus generator 125 to adjust the amount of electric current provided to the neurostimulators 115a-b. The current stimulus generator 125 may generate different types of neurostimulation including train-of-four (TOF), single twitch (ST), double burst (DBS), post tetanic count (PTC), current range (e.g., 1-70 mA with 1 mA steps), pulse width/frequency (e.g., 100, 200, 300 µs, or 1 Hz, 2 Hz, etc.). Further, the types of neurostimulation may be chosen via a manual or an automatic stimulating mode. If a manual stimulating mode is chosen, then the user may input the desired neuromuscular stimulating types, current range, and pulse width and/or frequency via pressing button 180 of the host patient monitor 140, for example. Alternatively, if a touch-screen is used as the display unit (e.g., display unit 190 of host patient monitor 140), then user input may be provided via touch input to the touch-screen on the display unit.

If an automatic neurostimulation mode is chosen, microcontroller 123 of neuromuscular transmission monitor 110 may select a first neurostimulation type as its default setting, such as TOF stimulation, and based on the muscle response signals received from the EMG and KMG sensors, the microcontroller may determine the optimal neurostimulation type, and report the muscle response signals to the user by displaying graphs and numbers (e.g., via display unit 190 of host patient monitor 140). The display unit 190 may display the muscle response data/information to the user and may also include alarm signals/message for alerting the user of potential sensor error.

Additionally, neuromuscular transmission monitor 110 may be connected to a host patient monitor 140 through a communication link 141. Host patient monitor 140 may include memory 127, CPU 128, and control unit 129. Memory 127 may have similar functions as memory 121. Control unit 129 may include control buttons/knobs 180 and display unit 190. The control buttons and knobs of control unit 129 may be configured to allow for user input. The display unit 190 may be configured to receive touch input from a user.

The type of neuromuscular stimulating outputs may include train-of-four (TOF), single twitch (ST), double burst (DBS) and post-tetanic count (PTC). In one example, TOF may typically use four brief (between 100 and 300 µs) current pulses (generally less than 70 mA) at 2 Hz, repeated every 10 to 20 s as electrostimulation. The resulting twitches (i.e. muscle response) may be measured and quantified for electromyographic response via the EMG sensor or for kinemyographic response via the KMG sensor, for example. The first twitch (referred to as the T1 twitch) and the last twitch (referred to as the T4 twitch) are compared and the ratio of the last twitch to the first twitch may provide an estimate of the level of neuromuscular blockade (e.g., depth of anesthesia) experienced by the patient. The TOF ratio may range from 0 to 100%, for example. The electrical stimuli series may be spaced by ten or more seconds (generally 20 s is used to provide a margin of safety) to give a rest period for full restoration of steady state conditions, as faster stimulation results in smaller evoked responses. TOF is the most commonly used technique for monitoring the neuromuscular blockade in lightly-blocked patients as well in patients that are recovering from neuromuscular block. However, in deep muscle blockade condition (e.g., during deep sedation), the fourth twitch may be too weak to be detected and thus, may provide a TOF ratio of zero. In that case, the muscle response may be provided at TOF count (TC).

TC is a medium sensitivity technique used to measure the evoked muscle response (e.g., number of twitches) where there is a moderate degree of paralyzation. In one example, TC may be a measure of an actual number of muscle twitches from a series of four electrical pulses. TC may range from 0 up to 4, for example.

ST measurement comprises of a single electrical pulse of between 100 and 300 µs, repeated at intervals greater than or equal to one second. Typically, four seconds may be needed between stimuli to prevent upregulation and alteration of the true muscle response. A baseline value, T0, before the administration of muscle relaxant may be needed since ST measures the ratio of the latest measured muscle twitch compared to the T0 value. Therefore, this technique may not be a preferred method for measuring neuromuscular transmission in patients that are already paralyzed.

DBS may comprise two bursts of two to four stimulations given at high frequency and separated by a brief intermission. In one example, two groups of stimuli of three pulses each at 50 Hz, spaced by 750 ms, and repeated at once every 10 s may be applied to the patient. DBS may be quantified by taking the ratio of the height of the second response relative to the first response. The DBS method may be used when the patient is in deep sedation and when the TOF ratio or count does not provide reliable results.

PTC may be used in deep blockade to evoke a large stimulating output in order to produce a condition of tetany in the corresponding muscle. In one example, a five second long 50 Hz electrical stimulation followed by a three second resting period and then up to twenty-one ST impulses at one per second may be provided during PTC mode. The number of impulses that can be measured indicates the degree of blockade. In one example, the PTC value may range from 0 up to greater than 20.

Comparing the above mentioned neuromuscular stimulation types/modes, TOF may be typically less sensitive than PTC, but more sensitive than DBS and ST. PTC can be very uncomfortable and may only be repeated only once every five or more minutes. TOF mode may be more advantageous because as a ratio of concurrent pulse, it does not require a pre-recorded control value for comparison, and thus has immunity to changing baseline measurements unlike the ST. Therefore, unless other stimulation modes is picked by the user, TOF may be set as the default mode of stimulus, especially during the onset of neuromuscular block and neuromuscular block recovery conditions. In one example, a threshold muscle response value may be predetermined and if TOF stimulation mode does not provide an adequate muscle response then a second stimulation mode may be picked, for example by the microcontroller 123. In that case, Post-tetanic count (PTC) may be used in order to evoke muscle response in patients during deep muscle blockade.

EMG sensor 160 may include a plurality of electro-sensing connections 116, 117, and 118 connected to sensing electrodes 120c, 120d, and 120e, respectively. Most commonly, the three sensing electrodes are positioned to give the most consistent EMG signals. In the depicted example, sensing electrode 120e is placed over the muscle tendon or finger, sensing electrode 120d is placed over the mid-portion of the muscle close to the neuromuscular junction, while sensing electrode 120c may be variable. In one example, electrodes 120d and 120e may be recording electrodes, while electrode 120c may be a grounding electrode. The grounding electrode provides a common reference for the EMG recording electrodes. For example, the recording electrode 120d may be placed on top of m. adductor pollicis in the thenar eminence and recording electrode 120e may be placed on top of the distal interphalangeal joint of the thumb, while the grounding electrode 120c may be placed at centerline over the flexor retinaculum at the palmar side of the wrist. EMG sensor 160 measures the magnitude of electrical activity sensed by electrodes 120c-120e in response to nerve stimulation and when received at the neuromuscular transmission monitor, is recorded as the EMG muscle response signal.

KMG sensor 150 includes a mechano-sensing connection 114 connected to bending element 119. In the depicted example, bending element 119 is placed between the thumb and the forefinger held in place by an elastic tape 127. The bending element 119 may comprise a piezoelectric polymer film which creates an electrical current in response to movement of any part of the polymer. When compressed or distorted, piezoelectric materials produce a charge proportional to the degree of alteration in shape. In FIG. 1, when the motor nerve is stimulated, thumb movement may cause a shape distortion in bending element 119 which in turn produces an electrical signal transmitted by mechano-sensing connection 114 and recorded at the monitor as a KMG muscle response signal.

Stimulating electrodes 120a-120b and sensing electrodes 120c-120e may have mechanisms for improving electrical contact to skin such as ultrasound gel and mechanisms for improving fixation to the skin such as biocompatible adhesives placed beneath the electrodes. Further, the electrodes may be suitable electrodes, such as silver/silver chloride electrodes. Further, the electrodes may be disposable electrodes which can be discarded after a single use. In another example, the stimulators (e.g., stimulators 115a and 115b) and the sensing connections (e.g. electro-sensing connections 116-118, and mechano-sensing connection 114) along with their respective electrodes may be incorporated into a disposable sensing unit. In one example, the disposable sensing unit may be included as part of a one-size-fits-all stretchable glove which may be discarded after a single use.

Further, information regarding the EMG and KMG muscle response signals received from EMG sensor 160 and KMG sensor 150, respectively, may be sent to neuromuscular transmission monitor 110 via main connector 113 and cable 112. In one example, muscle response signals from EMG sensor 160 and KMG sensor 150 may be differentiated and further fed into a signal scaling and filtering circuit (not shown). After scaling the signal and filtering noise, the signal may be converted from an analog signal to a digital signal in analog-to-digital (A/D) converter 122 and sent to a microcontroller 123 for processing. Further, the muscle response signals may also be amplified via an amplifier (not shown) before being transmitted into the A/D converter 122. The microcontroller 123, or processing unit, is connected to a memory 121 and once the signals are processed, the signal data may be displayed on the display unit 190 of the host patient monitor. In one example, the processed signals may be transmitted to the host patient monitor 140 and displayed on the display unit 190 in real-time. Further still, the processed signals may be updated and stored in memory 121. Memory 121 may be a conventional microcomputer which includes: a central processing unit (CPU), a read-only memory (ROM), a random access memory (RAM), and a conventional data bus. Memory 121 may further include a look-up table to convert neuromuscular response value between different stimulus modes. For example, the look-up table may include conversion data for TOF ratio format, TOF count format, PTC value format, DBS value format, and ST value format. The look-up table may also include conversion data for a normalized twitch amplitude, ST, PTC, TOF, and DBS measurements. Additionally, the memory may include an automatic calibration module to determine the optimum supramaximal current to provide to the patient based on the muscle response value received by the EMG and KMG sensors, and based on the raw signals received from each sensors, the module may determine a baseline value for each sensor, which may be used as a reference value for the neuromuscular blockade monitoring in patient. Further, the automatic calibration module may only be performed when patient is not in paralyzed state. In other words, the automatic calibration module may utilize a reference value based on the signals received from the sensors when patient is in non-relaxed state (e.g., before the administration of the muscle relaxant).

Further still, the microcontroller may be configured to detect errors in the signal received from any of the sensing electrodes (e.g., sensing electrodes 120c-120e for EMG sensor and sensing electrode (bending element 119) for KMG sensor). The microcontroller may detect errors such as out-of-range values (e.g., negative values) and alert the user that the electrodes may not be placed properly (e.g., if the electrodes become loose or detached from the skin).

Control unit 129 may also include a user interface (not shown) which can be used to control operation of the NMT monitoring system 100, including controlling the input of patient data, changing the monitoring parameters (e.g. stimulus type, current range, frequency/pulse width, etc.), and the like. The user interface may also include a graphical user interface configured for display on a display device, such as display unit 190. The graphical user interface may include information to be output to a user (such as muscle response signals, patient data, etc.) and may also include menus or other elements through which a user may enter input the control unit 129.

Further, CPU 128 may process the input provided by the user and command a constant current source stimulus generator 125 to provide a stimulus waveform and current depending on the selected stimulus mode, current range and pulse width/frequency. The neurostimulation type may be changed according to the patient's current and overall state of neuromuscular blockade. Further, a conversion module may be provided to convert muscle response value from a non-TOF stimuli into corresponding TOF data. For example, the conversion from PTC to TOF may be mapped using a linear or sigmoidal relationship model, and displayed as a TOF value on the display unit. In another example, the conversion module may further include a duration where a PTC evoked muscle responses may be measureable by TOF stimulation (e.g., if a PTC of 1 is measured, the conversion module may indicate that TOF may be measurable in 12 minutes).

If the automatic stimulating mode is chosen, the microcontroller may decide on the types of stimulus modes based on the muscle response signals received by the EMG and KMG sensors. For example, the microcontroller may be configured to run the default stimulus type, e.g., TOF, at the onset of the monitoring. However, if after a pre-determined duration (e.g. 30 s), inadequate muscle response reading are recorded, then the next stimulation type, such as PTC, may be chosen and applied (e.g., during deep sedation condition). At the same time, the microcontroller may also compare the two muscle response values collected from EMG and KMG sensors and determine a baseline value based on the comparison. For example, if the patient is already paralyzed during an emergency procedure before the NMT monitor is able to determine a reference baseline value (e.g., prior to the administration of muscle relaxant), then based on the default stimulus type setting (e.g., TOF), a muscle response value may be measured by the EMG and KMG sensors. In one example, TOF may be used to first determine a respective TOF ratio from each of the EMG and KMG sensors, and if the TOF ratios are zero, then TOF count may be displayed. Once the values are stabilized (e.g., when the same values are measured for a duration), the microcontroller may determine if the muscle response detected by the KMG sensors (also referred herein as KMG response) has reached below a threshold. The threshold may be a pre-determined number set by the manufacturer from a known value which represents the level of muscle paralysis in patient that is safe for performing intubation, for example. In another example, the threshold may be a non-response value determined based on the patient's thumb muscle movement upon nerve stimulation. When the EMG sensor reading differs from KMG sensor reading, the microcontroller may determine the maximum value for the EMG responses that correlates to the KMG non-response value, and further set the EMG baseline based on the new maximum value and the old EMG baseline value. If the new maximum value is higher than the old EMG baseline value, then the new maximum value may be recorded as the new EMG baseline value. Otherwise, the old EMG baseline is set as the baseline for EMG sensors. EMG responses may then be corrected by subtracting the numbers with the set EMG baseline values.

Turning now to FIG. 2, an example method 200 for determining a baseline muscle response in a paralyzed patient is shown. Method 200 may be carried out according to instructions stored on a computing system, including but not limited to the microcontroller 123 of the NMT monitoring system of FIG. 1. Method 200 may only be executed when the EMG and KMG sensors are securely connected to their respective electrodes on the patient's forearm, such as shown in FIG. 1. For example, when the patient is lying in a supine position with the stimulating electrodes placed on top of the ulnar nerve on the forearm, the electro-sensors attached to the sensing electrodes placed on the m. adductor pollicis in the thenar eminence, and the mechano-sensor attached to the sensing electrodes placed on top of the distal interphalangeal joint of the thumb on the same hand of the patient.

Method 200 includes, at 202, determining whether neuromuscular blocking agent (NMBA) has been administered. The method may further include displaying a message, such as "NMBA injected?" or "Has NMBA been injected?" to the user and requesting for user input. In one example, the requested user input may comprise of choosing between a "YES" and "NO" answer. Further, the user may provide an answer by pressing a button on the host patient monitor (e.g., button 180 of FIG. 1). If a touch-screen is used as the display unit (e.g., display unit 190 of control unit 129 of FIG. 1), then user input may be provided via touch input to the touch-screen on the display unit. If no NMBA has been injected, then the method proceeds to 224, where non-relaxed baseline values are determined based on a normal patient calibration routine.

In one example, the normal patient calibration routine may commence once anesthesia has been induced and after the patient has lost consciousness, but prior to the administration of the muscle relaxant (e.g. non-depolarizing NMBA). The NMT monitor may start by scanning a current level for supramaximal nerve stimulation (e.g., by using the automatic calibration module stored in the microcontroller memory). Once a stable muscle response level is recorded by the sensors (e.g., by waiting for a specified duration of time, such as 30 seconds), a supramaximal nerve stimulation is provided to the ulnar nerve and non-relaxed muscle response baseline values may be determined (e.g., T1 value when TOF mode is used), by the respective sensors. In one example, respective T1 values sensed by the EMG sensors and KMG sensors may be recorded separately such the muscle response reading from each sensor may be calibrated based on its own non-relaxed baseline value. Once the non-relaxed muscle response value is recorded, NMBA may then be injected into the patient to provide neuromuscular blocking and the muscle response values measured by the EMG and KMG sensors may then be calibrated against the non-relaxed muscle response baseline value, and the method ends.

If the user input indicates that NMBA has been administered, then the method proceeds to 204, where a baseline value for each of the KMG and EMG sensors in the paralyzed patient is determined by applying electrostimulation. The electrostimulation may be provided via neurostimulators coupled to the NMT monitoring system, such as neurostimulators 150a-b of FIG. 1. In one example, the amount of current, pulse width, and type of electrostimulation may be selected based on the user input (e.g., via selecting manual mode on the display screen or pressing a button on the NMT monitoring system). Further, if TOF ratio is detected as zero (e.g., if the fourth twitch, T4, has already disappeared), then the number of TOF count may be provided. Further still, if TOF count value is zero, such as when the first twitch T1 has disappeared, then PTC may be selected as the stimulus mode.

At 206, the muscle response is measured simultaneously with the KMG and EMG sensors. In one example, the muscle movement may be simultaneously detected by the distortion in piezoelectric material of the bending element of the KMG sensor (e.g. bending element 119 of FIG. 1) and the action potential of the muscle activity may be measured by the sensing electrodes of the EMG sensor (e.g. sensing electrodes 120c-120e of FIG. 1). The two muscle response values may then be optionally displayed on the display screen for monitoring. In one example, the muscle response in the paralyzed patient may be displayed as TOF count when T1% value is less than 10%, since TOF % value may not be accurate.

As mentioned previously, when the patient is already paralyzed, the normal calibration routine of the NMT monitoring system is not able to be performed since the neuromuscular blocking activity may have already been initiated, and thus a non-relaxed baseline value may not be established. In order to determine a non-response baseline value for the paralyzed patient, a baseline value may be set based on sensor output. In one example, the baseline for the EMG sensor may be defined based on the non-response KMG sensor measurements.

At 210, the TOF count from KMG sensor is calculated and, at 208, the TOF count from EMG sensor is also calculated. In one example, the TOF count from EMG and KMG sensors may be calculated simultaneously. Once the TOF counts from EMG and KMG sensors are calculated, the method proceeds to 212. While the example described herein with respect to FIG. 2 includes calculating TOF counts, it is to be understood that other mechanisms for determining the response to the neurostimulation may be used without departing from the scope of this disclosure.

At 212, it may be determined whether the KMG TOF count is less than the EMG TOF count. If the KMG TOF count is less than the EMG TOF count, then it may be determined that the EMG response is inaccurate (since no thumb movement is detected via the KMG sensor) and an EMG baseline correction may be applied. In order to ascertain that the response value acquired by the EMG sensor is accurate, the microcontroller may be configured to determine a baseline response for the EMG sensor based on non-response output values from the KMG sensor. In one example, the non-response KMG values may be determined when no muscle movement is measured by KMG sensors, such as when the KMG sensor reading is displayed as zero values (e.g., the TOF count from the KMG sensor is zero).

At 214, a maximum value of the EMG responses that correlate to non-response KMG measurements may be defined. In one example, the maximum value may be the highest value of the T1-T4 response values measured by the EMG sensor upon each TOF stimulation, when the KMG sensor detects no muscle movement in the patient's thumb (also referred herein as non-response values). Further, the non-response value KMG value may be displayed as zero to the user. Once the maximum value is determined, then the method proceeds to 216.

At 216, the EMG baseline is defined based on the new maximum value and an old (e.g., prior) EMG baseline value. In one example, the prior EMG baseline value may be retrieved from the microcontroller. Further, if it is determined that the new maximum value is less than the prior EMG baseline value, then the EMG baseline may be maintained as the prior EMG baseline value. Once the new maximum value exceeds the prior EMG baseline value, then the new EMG baseline may be defined based on the new maximum value. Once the EMG baseline is determined then the method may proceed to 218.

At 218, the EMG response is corrected by subtracting the EMG baseline from the currently-measured EMG response value. In one example, EMG measurement may be corrected by subtracting the baseline EMG value from each measured value of T1, T2, T3, and T4. Once the EMG responses are corrected based on the EMG baseline, a corrected TOF ratio and/or TOF count may be calculated. Based on the corrected TOF ratio or TOF count, various actions may be taken, such as outputting a representation of the corrected TOF count for display on a display device, alerting a user regarding block recovery based on the corrected TOF count, and so forth, which will be explained in more detail below with respect to FIG. 3. The method then ends.

Thus, according to the method illustrated in FIG. 2, a first stimulation is applied to a nerve of a patient, such as in the form of a TOF stimulation. Following the first stimulation, a first signal having a first value from a first neuromuscular transmission (NMT) sensor is received and a second signal having a second value from a second NMT sensor is received. In an example, the first NMT sensor may be a KMG sensor and the first value of the first signal may be a first TOF count calculated from the output of the KMG sensor. The second NMT sensor may be an EMG sensor. If it is determined that the first value is less than or equal to a threshold value, the second value may be set as a baseline value for the second NMT sensor. For example, if the first TOF count calculated from the output of the KMG sensor is zero, it may be determined that the KMG sensor is detecting no response from the patient. As such, any response values detected by the EMG sensor at that time may be due to electrical interference or other noise. Accordingly, the second value may be set as the baseline value for the EMG sensor, which may then be used to correct the output of the EMG sensor. The second value of the second signal from the EMG sensor may be the highest of the four response values (e.g., T1-T4) measured in response to the nerve stimulation.

Subsequently, a second stimulation may be applied to the nerve of the patient. Following the second stimulation, the second signal is again from the second NMT sensor. The second signal (e.g., the output from the EMG sensor) may have at least a third value. This third value may then be corrected based on the baseline value. For example, the baseline value may be subtracted from the third value to generate a corrected third value.

As the KMG sensor measures muscle movement through the bending of the thumb, the muscle response detected by the KMG sensor may have less interference than the EMG sensor. However, the KMG sensor is known to be less sensitive in detecting small movement, especially when patient is in deep sedation. Thus, by determining the EMG non-response baseline value based on non-response KMG value, the subsequent EMG responses may be subtracted with the EMG baseline value, which may substantially improve the signal-to-noise ratio of the EMG sensor and provide a more reliable neuromuscular monitoring to the paralyzed patient.

The non-response baseline value may differ from patient to patient since the amplitude of muscle movement may be affected by multiple factors, such as age, gender, amount of skin impedance (i.e. fat content under the skin), etc. Most neurostimulation utilizes a baseline which acts as a reference value for determining the level of muscle paralysis during a surgical procedure as well as for calculating the recovery times for the patient once the surgery has been completed.

By setting a baseline value for the muscular response of the paralyzed patient based on the EMG and KMG sensors, a more accurate neuromuscular response measurement may be obtained and used as a baseline reference value for all subsequent measurements. Further, the level of neuromuscular block from the subsequent readings may be compared with the baseline value which enables follow-up and prediction of neuromuscular block recovery which may help in correct timing of the antagonists, and further decrease the incidence of residual paralysis.

Referring now to FIG. 3, an example method 300 for monitoring neuromuscular transmission in a paralyzed patient during a surgical procedure is shown. Method 300 may be carried out according to instructions stored on a computing system, including but not limited to the microcontroller 123 of the NMT monitoring system of FIG. 1. Method 300 may be performed once a reference baseline value is determined for each KMG and EMG sensor (elaborated previously with respect to FIG. 2).

At 302, it is determined if the detected EMG and KMG responses are less than their respective baseline values. If the EMG and KMG responses are less than their respective baseline values, then the method proceeds to 306. Otherwise, if the EMG and KMG responses are not below their respective baseline values, then the method proceeds to 303 where the monitoring of the neuromuscular response of the patients via EMG and KMG sensors is continued. Further, in some examples, if the EMG sensor response and/or KMG sensor response are below respective baseline values, the user may be notified to adjust the amount of neuromuscular block administered to the patient.

At 306, the neuromuscular response of the intubated patient is monitored simultaneously via the KMG and the EMG sensors. In one example, the response values detected by both sensors may be normalized to their respective baseline values (e.g., by subtracting the baseline value from the measured response value or by determining a ratio of the measured response value to the baseline value) and then both normalized values may be displayed on the display unit. For example, both the TOF ratio and/or TOF count may be displayed for each sensor. In another example, if a non-TOF neurostimulation is used, then the response may be converted to TOF value (e.g., via a conversion module). Alternatively, an average value from the two sensors may be calculated such that only one value is displayed on the display unit.

At 308, it may be determined if the KMG response and/or EMG response values are over a limit. In other words, it may be determined if, during the monitoring, an error in the reading is detected (such as error detected by the error detecting circuit of FIG. 1). The limit may be a range of values which represent abnormal numbers, such as negative values or any values which are smaller/larger than the detection limit of the sensors. If the response values are over the limit, then the method proceeds to 318, where an error in the sensor reading is indicated. The method may further include notifying the user to check on the EMG and EKG sensor connections. In one example, the probable source of error may be shown to the user, by displaying a message that specifies detached electrodes or the like (e.g., when one or more of the sensing electrodes 120*c-e* of EMG sensor may have been detached from the skin of the patient, or when the tape (tape 127 of FIG. 1) which secured the bending element of KMG sensor may have been detached/removed). If the KMG and EMG responses are not out of a pre-determined range, then the method proceeds to 310.

At 310, it may be determined if the currently-obtained EMG value is higher than a threshold value. In one example, the threshold value may be the internal limit of the EMG sensor. In one example, the internal limit may be the detection limit of the EMG sensor. Since EMG reading is known to be more sensitive that the KMG reading, the neuromuscular monitoring of the patient during a surgery procedure may be solely based on the EMG response, provided that a baseline value has been determined prior to the monitoring (such as via routine 200 or normal calibration routine of FIG. 2). The KMG sensor, in this case, may be used as a secondary neuromuscular sensor to confirm the results acquired by EMG sensor, such as during recovery period. If the EMG value is not higher than the threshold value, then the method proceeds to 311 where the monitoring of neuromuscular response via EMG and KMG sensors are continued.

If it is determined that the EMG response is higher than the threshold value, then it may be possible that the effect of the muscle relaxant is diminishing, and the method then proceeds to 312, where it may be determined if the KMG response is higher than a threshold value. The threshold value may be based on the internal limit of the KMG sensor. The internal limit of the KMG sensor may be set as the detection limit of the sensor. Additionally, determining if KMG response is higher than the threshold value may further include visually detecting thumb movement in response to the neurostimulation. For example, if a user visually detects thumb movement, the user may enter input into the NMT monitoring system indicating thumb movement was detected. If the KMG response is not higher than the threshold, then the response value may be indicated as the non-response value and displayed to the user as zero and the method may then proceeds to 313 where EMG sensor degradation and/or EMG connection issues may be indicated, e.g., via a notification output to the user. In one example, the NMT monitoring system may include discarding the values detected by EMG sensor and only use KMG sensor as the main neuromuscular monitoring sensor for the patient. The method then proceeds to 311, where the neuromuscular monitoring via the KMG sensor is continued.

If the KMG sensor is higher than the threshold, then it may be confirmed that the patient is in recovery mode, and the method proceeds to 314, where a notification may be provided to the user indicating that the patient is in block recovery mode. The method may further include indicating to the user, at 315, to either adjust an amount of neuromuscular block provided to the patient (e.g., by increasing the NMBA dosage) if the surgical procedure has not been completed or, at 316, indicating to the user to add an antagonist and/or perform extubation when the surgical procedure has been completed.

In one example, additional neuromuscular block may be administered to the patient such that the muscle response goes to the EMG and/or KMG baseline when the patient is still in a middle of a surgery. Alternatively, if the surgical procedure has been completed and the patient neuromuscular block should be reversed, then an antagonist (also referred herein as neuromuscular block reversal agent) may be administered. Further, once the neuromuscular response reaches a pre-determined value (e.g., when TOF %>90%), then extubation may be performed.

By monitoring neuromuscular response with a combination of EMG and KMG sensors, an accurate estimate of the muscle strength may be determined, which may further allow an adequate reversal to be performed during recovery period. In this way, residual paralysis effects of the anesthetic agents may be avoided. Further, a reliable neuromuscular monitoring may be provided to paralyze patient via automatic measuring of a non-response baseline value based on the results from the two different neuromuscular sensors.

Referring now to FIG. 4, an example neuromuscular monitoring operating sequence is shown. Map 400 depicts neuromuscular response in EMG TOF % and EMG TOF count at plot 402 and 403, respectively, which may be determined from EMG T1-T4 sensor readings, selected examples of which are shown in plot 404. Map 400 further depicts neuromuscular response in KMG TOF % and KMG TOF count at plot 406 and 407, respectively. Further, based on the non-response values of the KMG sensor, the EMG TOF % and TOF count are corrected and shown in plot 408 and 411, respectively, which are calculated from corrected EMG T1-T4 sensor readings, selected examples of which are shown in plot 410. All plots are depicted over time along the x-axis. Time markers t1-t4 depict time points of significance during NMT monitoring.

NMT monitoring may be initiated at t0 when the patient is already paralyzed. In this case, a non-relaxed muscle response baseline may not be determined. Thus, once measured neuromuscular response from the EMG sensor differs from the measured neuromuscular response from the KMG sensor, an EMG baseline value may be defined based on KMG non-response value, and the EMG baseline may be used to correct the EMG responses.

In the depicted example, the TOF % and TOF count values at t0 are similar between the EMG and KMG sensors, and thus, no baseline correction is needed. At t1, the EMG sensor starts to output a measurable response signal as shown in plot 402 and 403. However, no responses are measured by the KMG sensor at t1 (as shown in plot 406 and 407). Thus, it may be determined that the EMG sensor is subject to measurement interference and an EMG baseline correction is applied.

The EMG maximum value that correlates to the non-response KMG measurement may then be determined by the microcontroller and the EMG baseline is then defined based on the new maximum value and an old (e.g., prior) EMG baseline value. If the new maximum value is larger than the old EMG baseline value, then the EMG baseline value may be set according to the new maximum value. However, if the new maximum value is less than the old EMG baseline value, then the old EMG baseline value may be set as the baseline for EMG sensor.

EMG responses, such as TOF % and TOF count, are then corrected by subtracting the EMG baseline from one or more EMG response values (e.g., TOF % and TOF count), as shown in plot 408 and 411, respectively. For example, a first TOF % 401 from the EMG sensor following time t1 is calculated from EMG TOF sensor values (shown in plot 404). The T1 and T4 readings are similar, and thus the TOF % is relatively high, such as 99%, and the TOF count for the EMG sensor is four. However, at that same time, the TOF % and TOF count from the KMG sensor may be undetectable (e.g., zero). Thus, a baseline EMG value may be determined that is the highest of the T1-T4 readings taken to determine the TOF % 401 (e.g., the value of T1 may be set as the baseline value). The EMG sensor output may be corrected by the baseline value. For example, the baseline EMG value may be subtracted from each value of the T1-T4 readings to generate corrected T1-T4 readings. As the baseline EMG value is the highest of the T1-T4 readings, the corrected EMG TOF values are all zero. A corrected TOF % and TOF count is then determined from the corrected T1-T4 readings such that both the EMG TOF % and EMG TOF count are zero immediately following time t1.

At t2, the KMG sensors begins to detect muscle movement as depicted by the increase in TOF % values (plot 406) and TOF count values (plot 407). Since the KMG sensor no longer detects a non-response value at t2, the EMG response correction may be based on the previously determined EMG baseline value where KMG sensor did not detect muscle movement (e.g., the KMG non-response values). In one example, the EMG response at t2 may be corrected based on the baseline defined at t1.

For example, an EMG TOF % 405 may be determined from the corresponding EMG TOF T1-T4 values shown in plot 404 (e.g., the second set of values). However, because the KMG sensor is outputting positive/detectable values, a prior EMG baseline value is used to correct the EMG sensor output, such as the baseline value calculated at time t1 (e.g., a value of 100). When the baseline is subtracted from each of the T1-T4 values, a set of corrected EMG T1-T4 values are generated, as shown in plot 410. The corrected EMG TOF % and TOF count are determined from the corrected EMG TOF values.

Following t3, the KMG sensor does not determine any muscle movement and thus the EMG baseline may again be determined from the currently-measured EMG response values (e.g., at the time of the non-response value of KMG sensor). Further, EMG responses at t3 may then be corrected by subtracting the determined EMG baseline from the measured T1-T4 response values.

At t4, both the EMG and KMG sensors detect a similar response (e.g. zero TOF % and TOF count). Thus, at this time, no EMG baseline correction is needed and the EMG responses may be displayed without subtracting the baseline value.

Referring now to FIG. 5, example T1-T4, TOF %, TOF count values are shown for the EMG sensor, KMG sensor, and a corrected EMG sensor. Map 500 further depicts raw output values of the EMG sensor (also referred herein as the electrosensor) at plot 502, raw output values of the KMG sensor (also referred herein as the mechnosensor) at plot 504, and corrected output values of the EMG sensor at plot 506. Row numbers on the y-axis depicts the neuromuscular response readings at each TOF stimulation monitored over time, with increasing time towards the direction of arrow.

Between rows 1-5, the KMG sensor detects no muscle movement on the patient's thumb, depicted as zero values at plot 504. However, the EMG sensor detects responses between rows 3-5, which may be due to high noise background attributed by other electrical equipment in the surgery room. In order to provide accurate neuromuscular monitoring, the EMG responses are corrected. Thus, a maximum value is determined for the EMG responses based on the non-response value of KMG sensor during each TOF stimulation. In one example, the value 98 is determined to be the maximum value for row 3 and 4 of the electrosensor. Similarly, for row 5, the value 100 is determined to be the maximum value of electrosensor. The EMG baseline value for each row may then be recorded and stored in the microcontroller memory, for example.

Once the EMG baseline is determined (right-most column of plot 502), the raw EMG output may then be corrected by subtracting the baseline from the T1-T4 values. As shown in row 3-5 of plot 506, once corrected, the EMG response shows similar values as the KMG responses (plot 504).

Between rows 6-13, KMG sensors detects some muscle movement as represented as non-zero values in plot 504. Thus, the EMG responses are corrected based on the last determined EMG baseline value where KMG reading equals to zero (e.g., EMG baseline determined at row 5). In this way, the EMG responses are subtracted by the EMG baseline determined based on KMG non-response values.

Similarly, between rows 14-18, the KMG sensor outputs zero values (e.g., non-response values). Therefore, the EMG baseline may again be determined by defining the maximum value detected by EMG sensor at each TOF stimulation. Since no value higher than 100 is detected between rows 14-16, no new EMG baseline is recorded. However, at row 17, the value 101 is detected, and since it is higher than the previous EMG baseline value, 101 is then recorded as the new EMG baseline for rows 17-18.

By accurately measuring neuromuscular response in a patient, optimal surgical conditions, such as deep neuromuscular block with TOF count <1, may be achieved. By employing a combination of KMG and EMG sensors, neuromuscular blockade monitoring may be improved by allowing automatic setting of EMG baseline values based on KMG values. A technical effect of the disclosure is to allow automatic determination of a non-response baseline value in a paralyzed patient and thus further enables the NMT system for adaptive learning to accommodate patient variance (e.g., setting different non-response baseline value based on patient's muscle activity) and further increases the reliability of the neuromuscular measurements during a surgical procedure.

An example provides a system including a stimulator; an electromyography (EMG) sensor; a kinemyography (KMG) sensor; and a single connector configured to couple each of the stimulator, the EMG sensor, and the KMG sensor to a patient monitoring device via a single input. In a first example of the system, the EMG sensor comprises a plurality of sensing electrodes, and the KMG sensor comprises a piezoelectric sensor. A second example of the system optionally includes the first example, and further includes the stimulator, the plurality of sensing electrodes, the piezoelectric sensor, and the connector are being housed on a common housing. A third example of the system optionally includes one or both of the first and second examples, and further includes the patient monitoring device being configured to activate the stimulator and subsequently receive a first signal from the EMG sensor and a second signal from the KMG sensor, each of the first signal and the second signal indicative of muscle activity of a patient responsive to nerve stimulation of the patient resulting from the activation of the stimulator. A fourth example of the system optionally includes one or more or each of the first through third examples, and further includes the patient monitoring device being configured to determine a baseline response for the EMG sensor based on output from the KMG sensor. A fifth example of the system optionally includes one or more or each of the first through fourth examples, and further includes the patient monitoring device being configured to display a representation of the first signal along with a representation of the second signal.

Another example provides a method including applying a first stimulation to a nerve of a patient; following the first stimulation, receiving a first signal having a first value from a first neuromuscular transmission (NMT) sensor and receiving a second signal having a second value from a second NMT sensor; determining that the first value is less than or equal to a threshold value, and in response, setting the second value of the second signal as a baseline value for the second NMT sensor; applying a second stimulation to the nerve of the patient; following the second stimulation, receiving the second signal from the second NMT sensor, the second signal having a third value; and correcting the third value based on the baseline value. In a first example of the method, the first signal and the second signal are each indicative of muscle activity of the patient resulting from the stimulation. In a second example of the method, which optionally includes the first example, receiving a first signal from a first NMT sensor comprises receiving a first signal from a kinemyography (KMG) sensor, and receiving a second signal from a second NMT sensor comprises receiving a second signal from an electromyography (EMG) sensor. In a third example of the method, which optionally includes the first and/or second example, the method further includes taking an action based on the corrected third value, where the action comprises outputting a notification to a user responsive to the third value being above the baseline value by more than a predetermined amount. In a fourth example of the method, which optionally includes one or more or each of the first through third examples, outputting the notification comprises outputting a notification instructing the user to adjust an amount NMT blocker provided to the patient. In a fifth example of the method, which optionally includes one or more or each of the first through fourth examples, outputting the notification comprises outputting a notification instructing the user to initiate an extubation procedure. In a sixth example of the method, which optionally includes one or more or each of the first through fifth examples, the method further includes taking an action based on the corrected third value, the action including outputting a notification to a user responsive to the third value being within a predetermined range of the baseline value for a predetermined amount of time. In a seventh example of the method, which optionally includes one or more or each of the first through sixth examples, the method further includes taking an action based on the corrected third value, the action including outputting a representation of the corrected third value for display on a display device. In an eighth example of the method, which optionally includes one or more of each of the first through seventh examples, the representation is a first representation and the method further comprises outputting a second representation of a subsequent, fourth value of the first signal for display on the display device.

Another example provides a method including applying a train-of-four (TOF) stimulation to a nerve of a patient; determining respective KMG T1, T2, T3, and T4 values from a kinemyography (KMG) sensor resulting from the TOF stimulation and determining respective EMG T1, T2, T3, and T4 values from an electromyography (EMG) sensor resulting from the TOF stimulation; determining that a KMG TOF count is zero and that an EMG TOF count is greater than zero, and in response, setting a baseline value for the EMG sensor to be a highest of the respective EMG T1, T2, T3, and T4 values; correcting the respective EMG T1, T2, T3, and T4 values based on the baseline value and calculating a corrected EMG TOF count; and displaying on a display device a first representation of the corrected EMG TOF count. In a first example of the method, the method further comprises: applying a second TOF stimulation to the nerve of the patient; determining respective second KMG T1, T2, T3, and T4 values from the KMG sensor resulting from the second TOF stimulation and determining respective second EMG T1, T2, T3, and T4 values from the EMG sensor resulting from the second TOF stimulation; calculating a second KMG TOF count from the respective second KMG T1, T2, T3, and T4 values and calculating a second EMG TOF count from the respective second EMG T1, T2, T3, and T4 values; determining that the second KMG TOF count is greater than zero and that the second EMG TOF count is greater than zero, and in response, maintaining the baseline value; correcting the respective second EMG T1, T2, T3, and T4 values based on the baseline value and calculating a second corrected EMG TOF count; and displaying on the display device a second representation of the second corrected EMG TOF count. In a second example of the method, which optionally includes the first method, the method further comprises: responsive to each of the second KMG TOF count and second corrected EMG TOF count being above a recovery threshold, outputting a notification to a user instructing the user to adjust an amount of a neuromuscular transmission block provided to the patient. In a third example of the method, which optionally includes one or both of the first and second examples, the method further includes, responsive to only the corrected EMG TOF count being above the recovery threshold, outputting a notification to the user indicating degradation of the EMG sensor.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for a neuromuscular transmission (NMT) system including a controller, comprising:
   applying a first stimulation to a nerve of a patient;
   following the first stimulation, receiving, at the controller, a first signal having a first value from a first NMT sensor and receiving, at the controller, a second signal having a second value from a second NMT sensor;
   determining, via the controller, that the first value is less than or equal to a threshold value, and in response, setting the second value as a baseline value for the second NMT sensor and storing the baseline value in memory of the NMT system;
   applying a plurality of additional stimulations to the nerve of the patient;
   following each additional stimulation, receiving, at the controller, the second signal from the second NMT sensor, the second signal having a signal value;
   correcting, via the controller, each signal value based on the baseline value stored in memory; and
   displaying each corrected signal value on a display device of the NMT system.

2. The method of claim 1, wherein the first signal and the second signal are each indicative of muscle activity of the patient resulting from the stimulation.

3. The method of claim 1, wherein receiving the first signal from the first NMT sensor comprises receiving a first signal from a kinemyography (KMG) sensor, and wherein receiving the second signal from the second NMT sensor comprises receiving a second signal from an electromyography (EMG) sensor.

4. The method of claim 1, wherein the baseline value is a first baseline value and, further comprising:
   determining that a most-recently received signal value is greater than the baseline value and that a most-recently received value from the first NMT sensor is less than or equal to the threshold value; and
   in response, updating the first baseline value to a second baseline value based on the most-recently received signal value.

5. The method of claim 1, further comprising outputting a notification to a user responsive to one or more of the corrected signal values being above a recovery threshold.

6. The method of claim 5, wherein outputting the notification comprises outputting a notification instructing the user to adjust an amount of NMT blocker provided to the patient.

7. The method of claim 5, wherein outputting the notification comprises outputting a notification instructing the user to initiate an extubation procedure.

8. The method of claim 1, wherein correcting each signal value based on the baseline value comprises, for each signal value, subtracting the baseline value from that signal value to determine a corrected signal value.

9. The method of claim 1, further comprising displaying a subsequent, fourth value of the first signal on the display device.

10. A method, comprising
applying a train-of-four (TOF) stimulation to a nerve of a patient;
determining respective KMG T1, T2, T3, and T4 values from a kinemyography (KMG) sensor resulting from the TOF stimulation and determining respective EMG T1, T2, T3, and T4 values from an electromyography (EMG) sensor resulting from the TOF stimulation;
determining that a KMG TOF count is zero and that an EMG TOF count is greater than zero, and in response, setting a baseline value for the EMG sensor to be a highest of the respective EMG T1, T2, T3, and T4 values;
correcting the respective EMG T1, T2, T3, and T4 values based on the baseline value and calculating a corrected EMG TOF count; and
displaying on a display device a first representation of the corrected EMG TOF count.

11. The method of claim 10, further comprising:
applying a second TOF stimulation to the nerve of the patient;
determining respective second KMG T1, T2, T3, and T4 values from the KMG sensor resulting from the second TOF stimulation and determining respective second EMG T1, T2, T3, and T4 values from the EMG sensor resulting from the second TOF stimulation;
calculating a second KMG TOF count from the respective second KMG T1, T2, T3, and T4 values and calculating a second EMG TOF count from the respective second EMG T1, T2, T3, and T4 values;
determining that the second KMG TOF count is greater than zero and that the second EMG TOF count is greater than zero, and in response, maintaining the baseline value;
correcting the respective second EMG T1, T2, T3, and T4 values based on the baseline value and calculating a second corrected EMG TOF count; and
displaying on the display device a second representation of the second corrected EMG TOF count.

12. The method of claim 11, further comprising, responsive to each of the second KMG TOF count and second corrected EMG TOF count being above a recovery threshold, outputting a notification to a user instructing the user to adjust an amount of a neuromuscular transmission block provided to the patient.

13. The method of claim 12, further comprising, responsive to only the corrected EMG TOF count being above the recovery threshold, outputting a notification to the user indicating degradation of the EMG sensor.

* * * * *